(12) United States Patent
Fujiwara (10) Patent No.: US 9,846,947 B2
(45) Date of Patent: Dec. 19, 2017

(54) MEDICAL IMAGE PROCESSING APPARATUS, X-RAY COMPUTERIZED TOMOGRAPHY APPARATUS, AND MEDICAL IMAGE PROCESSING METHOD

(71) Applicant: TOSHIBA MEDICAL SYSTEMS CORPORATION, Otawara-shi (JP)

(72) Inventor: Megumu Fujiwara, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 399 days.

(21) Appl. No.: 14/525,301

(22) Filed: Oct. 28, 2014

(65) Prior Publication Data
US 2015/0131772 A1 May 14, 2015

(30) Foreign Application Priority Data
Nov. 8, 2013 (JP) .................................. 2013-232433

(51) Int. Cl.
*G06T 7/20* (2017.01)
*G06T 15/20* (2011.01)
(Continued)

(52) U.S. Cl.
CPC .............. *G06T 7/248* (2017.01); *A61B 6/463* (2013.01); *A61B 6/486* (2013.01); *G06T 3/60* (2013.01);
(Continued)

(58) Field of Classification Search
CPC .... A61B 6/00; A61B 6/02; A61B 6/03; A61B 6/46; A61B 6/461; A61B 6/463; A61B 6/466; A61B 6/48; A61B 6/486; A61B 6/52; A61B 6/5211; A61B 2576/00; A61B 2576/02; G06T 1/00; G06T 1/0007; G06T 3/00; G06T 3/60; G06T 7/00; G06T 7/0012; G06T 7/0014; G06T 7/0016; G06T 7/10; G06T 7/11; G06T 7/149; G06T 7/174; G06T 7/20; G06T 7/215; G06T 7/223; G06T 7/231; G06T 7/238; G06T 7/246; G06T 7/248; G06T 7/251; G06T 7/70; G06T 7/73; G06T 7/74; G06T 7/75; G06T 7/97; G06T 15/00; G06T 15/08;
(Continued)

(56) References Cited

U.S. PATENT DOCUMENTS

| | | | |
|---|---|---|---|
| 8,848,998 B1* | 9/2014 | Muradyan | G06T 7/0016 382/131 |
| 2004/0249270 A1* | 12/2004 | Kondo | G06T 15/08 600/425 |

(Continued)

FOREIGN PATENT DOCUMENTS

JP 2013-172815 9/2013

*Primary Examiner* — Anastasia Midkiff
(74) *Attorney, Agent, or Firm* — Oblon, McClelland, Maier & Neustadt, L.L.P.

(57) ABSTRACT

A medical image processing apparatus according to the present invention includes a moving direction identification unit configured to identify a moving direction of an observed region of a subject depicted in a plurality of volume data collected by a medical diagnostic apparatus, each volume data of the plurality of volume data being collected for each time phase; and a display direction setting unit configured to set a display direction of the plurality of volume data based on the identified moving direction.

16 Claims, 9 Drawing Sheets

(51) Int. Cl.
*G06T 19/00* (2011.01)
*A61B 6/03* (2006.01)
*G06T 7/246* (2017.01)
*G06T 7/73* (2017.01)
*G06T 7/174* (2017.01)
*G06T 7/00* (2017.01)
*G06T 3/60* (2006.01)
*A61B 6/00* (2006.01)

(52) U.S. Cl.
CPC ............ *G06T 7/0016* (2013.01); *G06T 7/174* (2017.01); *G06T 7/20* (2013.01); *G06T 7/73* (2017.01); *G06T 7/97* (2017.01); *G06T 15/205* (2013.01); *A61B 6/032* (2013.01); *A61B 6/5264* (2013.01); *G06T 19/00* (2013.01); *G06T 2207/10076* (2013.01); *G06T 2207/10081* (2013.01); *G06T 2207/30008* (2013.01); *G06T 2210/41* (2013.01); *G06T 2211/40* (2013.01); *G06T 2219/008* (2013.01); *G06T 2219/2004* (2013.01); *G06T 2219/2016* (2013.01)

(58) Field of Classification Search
CPC ....... G06T 15/10; G06T 15/20; G06T 15/205; G06T 19/00; G06T 19/003; G06T 19/20; G06T 2200/00; G06T 19/04; G06T 19/08; G06T 19/21; G06T 19/28; G06T 2207/00; G06T 2207/10; G06T 2207/10072; G06T 2207/10076; G06T 2207/10081; G06T 2207/20; G06T 2207/30; G06T 2207/30004; G06T 2207/30008; G06T 2210/00; G06T 2210/41; G06T 2211/00; G06T 2211/40; G06T 2215/00; G06T 2219/00; G06T 2219/008; G06T 2219/20; G06T 2219/2004; G06T 2219/2016; H04N 5/30; H04N 5/32; H04N 5/335; H04N 5/44; H04N 5/341; H04N 5/345; H04N 5/3452; H04N 19/00; H04N 19/50; H04N 19/503; H04N 19/51; H04N 19/513; H04N 19/537; H04N 19/543; H04N 19/573; H04N 19/58; H04N 2201/00; H04N 2201/0001; H04N 2201/0426; H04N 2201/043

See application file for complete search history.

(56) References Cited

U.S. PATENT DOCUMENTS

2005/0017972 A1* 1/2005 Poole .................. A61B 5/7445
345/424
2009/0136106 A1* 5/2009 Roberts .................. G06T 15/08
382/130
2010/0088644 A1* 4/2010 Dowson ............... G06K 9/3233
715/837

* cited by examiner

MEDICAL IMAGE PROCESSING APPARATUS, X-RAY COMPUTERIZED TOMOGRAPHY APPARATUS, AND MEDICAL IMAGE PROCESSING METHOD

CROSS-REFERENCE TO RELATED APPLICATION

This application is based upon and claims the benefit of priority from Japanese Patent Application No. 2013-232433, filed on Nov. 8, 2013, the entire contents of which are incorporated herein by reference.

FIELD

An embodiment of the present invention relates to a medical image processing apparatus, an X-ray computerized tomography apparatus, and a medical image processing method.

BACKGROUND

Recently, medical diagnostic apparatus provided with high temporal resolution as well as three-dimensional spatial resolution and configured to be able to generate so-called 4D (4th Dimension) images have developed remarkably. Consequently, for example, in examinations using an X-ray computerized tomography apparatus, it is becoming common practice as a mode of examination to generate 4D images while moving a joint area of a subject such as a wrist or an ankle.

Normally, when a medical image such as a 4D image described above or a 2D (2-Dimensional) image or 3D (3-Dimensional) image collected by a medical diagnostic apparatus in a certain time phase is displayed on a monitor or the like, the medical image is displayed at first in a fixed viewing direction based on a posture of the subject. Then, an operator sets a display direction of the medical image using a rotation function of an application or the like, causing the medical image to be displayed in a desired viewing direction for the operator.

However, the conventional technique, which displays the medical image in a fixed viewing direction based on the posture of the subject, does not display the medical image in the desired viewing direction for the operator. This makes it necessary for the operator to adjust the display direction each time the operator observes a subject.

Thus, there is demand for a medical image processing apparatus, X-ray computerized, tomography apparatus, and medical image processing method which can easily display medical images in a display direction in which the operator wants to observe the images.

BRIEF DESCRIPTION OF THE DRAWINGS

In accompanying drawings.

DETAILED DESCRIPTION

To solve the above problem, a medical image processing apparatus according to an embodiment of the present invention comprises a moving direction identification unit configured to identify a moving direction of an observed region of a subject depicted by a plurality of volume data collected by a medical diagnostic apparatus, each volume data of the plurality of volume data being collected for each time phase; and a display direction setting unit configured to set a display direction of the plurality of volume data based on the identified moving direction.

First Embodiment

A first embodiment will be described below with reference to drawings. Note that a medical image processing apparatus will be described in the first embodiment.

First, a configuration of the medical image processing apparatus according to the first embodiment will be described with reference to FIG. 1.

Figure 1:
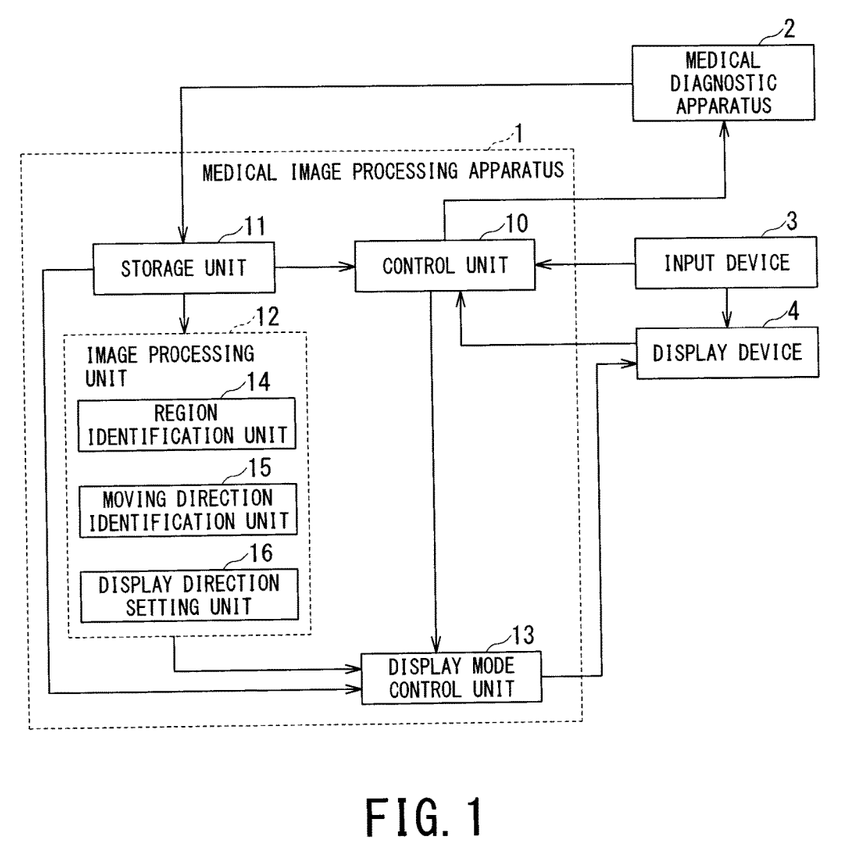
FIG. 1 is a block diagram of a medical image processing apparatus according to a first embodiment.

FIG. 1 is a block diagram of the medical image processing apparatus 1 according to the first embodiment.

The medical image processing apparatus 1 according to the first embodiment includes a control unit 10, a storage unit 11, an image processing unit 12, a display mode control unit 13, and the like. The medical image processing apparatus 1 is connected with a medical diagnostic apparatus 2, an input device 3, and a display device 4 by a wired or wireless method and configured to be able to exchange data and signals with these apparatus/devices.

The medical diagnostic apparatus 2 is, for example, an X-ray computerized tomography apparatus. For example, the medical diagnostic apparatus 2 has a function to collect volume data which represents an observed region containing a joint area such as a finger, a wrist, an elbow, a shoulder, the neck, an ankle, a knee, or the crotch of the subject every time phase. The medical diagnostic apparatus 2 has a function to transfer the volume data collected every time phase to the storage unit 11 of the medical image processing apparatus 1 on instructions from the control unit 10 of the medical image processing apparatus 1.

In the first embodiment, it is assumed that the volume data refers to image data in general depicted three-dimensionally. For example, it is assumed that the volume data includes data obtained by adding together sectional image data depicted two-dimensionally, in a slice direction perpendicular to a cross-section. Note that in the first embodiment, the smallest unit making up volume data is defined as a voxel, and a value each voxel has is defined as a voxel value. That is, for example, in the case of medical image data whose volume data is depicted two-dimensionally as described above, pixels and pixel values of the medical image data depicted two-dimensionally correspond to voxels and voxel values in the first embodiment.

The input device 3 is used by the operator and configured to input instructions to the control unit 10 of the medical image processing apparatus 1 based on input from the operator. Note that, in the first embodiment, the input device 3 is described, for example, as being a pointing device such as a mouse or track ball.

The display device 4 is a display unit configured to display image data on a monitor, display, or the like. The display device 4 has a function to display image data for display transferred from the display mode control unit 13. Also, the display device 4 has a function to transmit instructions entered through the input device 3 to the control unit 10 of the medical image processing apparatus 1.

The control unit 10 of the medical image processing apparatus 1 has a function to instruct the medical diagnostic apparatus 2 to transfer volume data according to instructions transmitted from the display device 4. When the volume data transferred from the medical diagnostic apparatus 2 is stored in the storage unit 11, the control unit 10 has a function to instruct the storage unit 11 to transfer the volume data to the image processing unit 12. Also, upon acquiring a notice from the image processing unit 12 to the effect that a display direction setting of the volume data has been completed, the control unit 10 has a function to instruct the storage unit 11 to transfer the volume data stored in the storage unit 11 to the display mode control unit 13.

The storage unit 11 of the medical image processing apparatus 1 has a function to store the volume data transferred from the medical diagnostic apparatus 2. The storage unit 11 has a function to transfer the volume data stored in the storage unit 11 itself to the image processing unit 12 according to instructions from the control unit 10. Also, the storage unit 11 has a function to transfer the volume data stored in the storage unit 11 itself to the display mode control unit 13 according to instructions from the control unit 10.

The image processing unit 12 of the medical image processing apparatus 1 includes a region identification unit 14, a moving direction identification unit 15, and a display direction setting unit 16. Also, the image processing unit 12 is equipped, for example, with a storage unit such as a memory (not shown). Respective processes performed by the region identification unit 14, moving direction identification unit 15, and display direction setting unit 16 are performed on volume data stored in the storage unit.

The region identification unit 14 of the image processing unit 12 has a function to identify those voxel regions in at least two the volume data transferred to the image processing unit 12 from the storage unit 11 which represent part or all of an observed region of the subject.

In the first embodiment, description will be given of a case in which the region identification unit 14 identifies voxel regions in all the volume data transferred to the image processing unit 12 from the storage unit 11. Also, in the first embodiment, description will be given of a case in which the region identification unit 14 identifies voxel regions which represent the subject's entire observed region in the volume data. Furthermore, the voxel region in the first embodiment does not always need to be made up of plural spatially consecutive voxels, and may be made up of a single voxel or plural voxels which are not spatially consecutive.

The moving direction identification unit 15 of the medical image processing apparatus 1 has a function to identify a moving direction of the observed region of the subject depicted in plural volume data collected by the medical diagnostic apparatus 2, each volume data of the plurality of volume data being collected for each time phase. For example, the moving direction identification unit 15 identifies a plane (hereinafter also referred to as a moving-direction plane) containing the moving direction of the subject's observed region depicted in the volume data transferred to the image processing unit 12 from the storage unit 11.

Here, the moving-direction plane means, for example, a plane on which the voxel regions which represent an observed region have large amounts of change or a strong changing tendency in the volume data corresponding to each time phase. As a specific example, for volume data in which voxel regions have been set by the region identification unit 14, the moving direction identification unit 15 calculates displacement of some or all of the voxel regions and identifies the moving-direction plane of the subject's observed region based on the calculated displacement. In the first embodiment, a case in which the moving direction and moving-direction plane of the observed region are identified by calculating the displacement among all the voxel regions will be described.

The display direction setting unit 16 of the medical image processing apparatus 1 has a function to set a display direction of plural volume data based on the moving direction of the observed region identified by the moving direction identification unit 15. For example, the display direction setting unit 16 sets a direction perpendicular to a plane including the moving direction identified by the moving direction identification unit 15 to the display direction of the plural volume data.

The image processing unit 12 has a function to notify the display mode control unit 13 of the display direction set by the display direction setting unit 16. Also, when the display direction is set by the display direction setting unit 16, the image processing unit 12 has a function to notify the control unit 10 to the effect that the display direction setting has been completed.

Upon being notified of the display direction by the image processing unit 12, the display mode control unit 13 of the medical image processing apparatus 1 has a function to control a display mode such that the display direction of the volume data transferred from the storage unit 11 will match the direction notified of by the image processing unit 12 and to transfer the volume data as image data for display to the display device 4.

Figure 2:
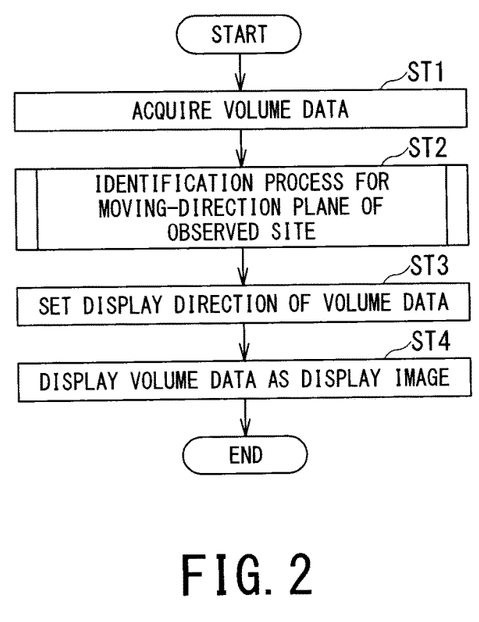
FIG. 2 is a flowchart outlining operation of the medical image processing apparatus according to the first embodiment.

Next, operation of the medical image processing apparatus 1 according to the first embodiment will be outlined with reference to a flowchart.

FIG. 2 is a flowchart outlining the operation of the medical image processing apparatus 1 according to the first embodiment.

First, the medical image processing apparatus 1 acquires plural volume data collected by the medical diagnostic apparatus 2, each volume data of the plurality of volume data being collected for each time phase and stores the acquired volume data in the storage unit 11 (step ST1).

Next, the image processing unit 12 of the medical image processing apparatus 1 acquires the plural volume data from the storage unit 11 and the moving direction identification unit 15 performs a process of identifying the moving-direction plane of the subject's observed region depicted in the volume data (step ST2).

The image processing unit 12 of the medical image processing apparatus 1 causes the display direction setting unit 16 to set a direction perpendicular to the moving-direction plane identified by the moving direction identification unit 15 to the display direction of the plural volume data (step ST3).

The display mode control unit 13 of the medical image processing apparatus 1 controls the display mode such that the display direction of the volume data transferred from the storage unit 11 will match the direction set by the image processing unit 12 and causes the display device 4 to display the volume data as a display image represented by the image data for display (step ST4).

As described above, the medical image processing apparatus 1 according to the first embodiment identifies the moving-direction plane of the subject's observed region in plural volume data collected chronologically and sets the display direction of the plural volume data based on the identified moving-direction plane.

Consequently, since the medical image processing apparatus 1 according to the first embodiment can display the volume data based on the moving direction of the observed region, the operator can easily check the medical image according to the display direction which is based on the moving direction of the desired observed region.

When observing motion of an observed region containing a joint area such as a finger, a wrist, an elbow, a shoulder, the neck, an ankle, a knee, or the crotch, it is possible to easily provide a display in the display direction suitable for observation.

Also, it becomes less likely that volume data viewed in a direction deviated greatly from a desired display direction, and consequently the operator can check the motion of the observed region simply by fine-tuning the display direction. This relieves the operator of labor and stress involved in adjusting the display direction of the volume data depicted three-dimensionally.

(Identification Process for Moving-Direction Plane of Observed Region)

Figure 3:
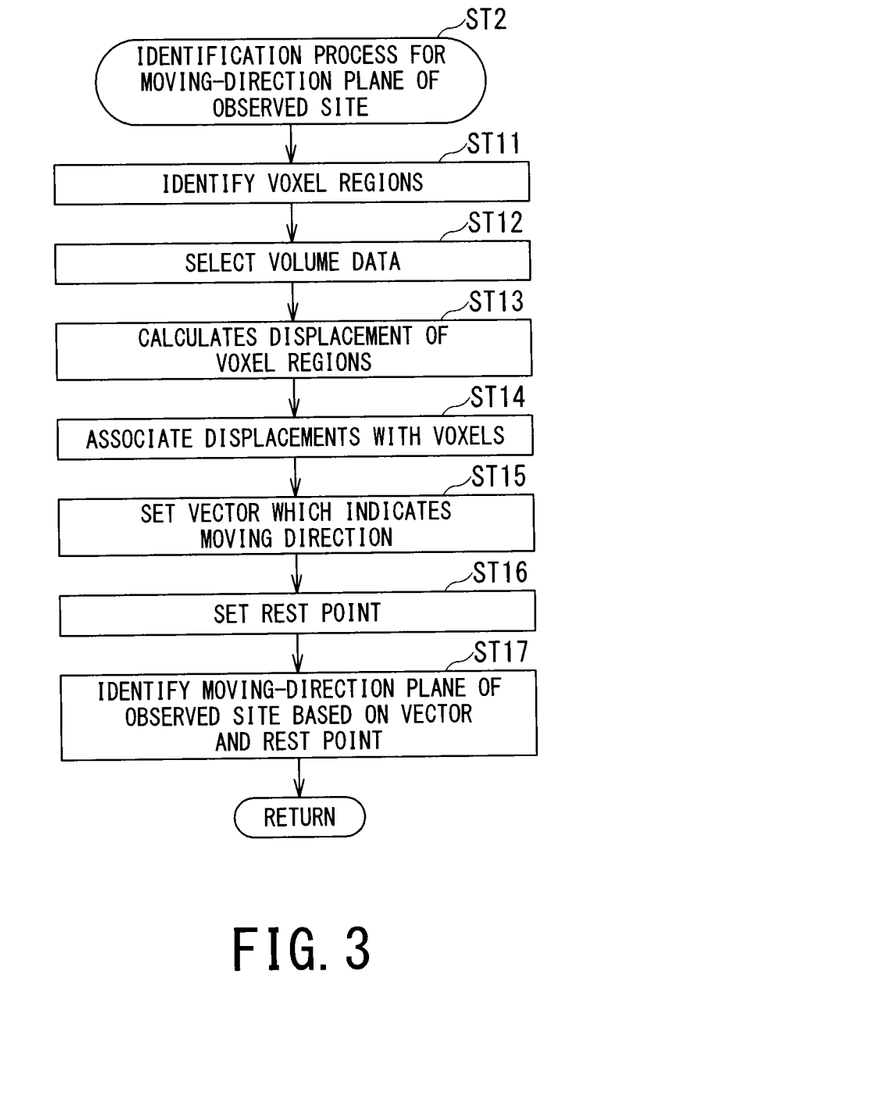
FIG. 3 is a flowchart showing an example of an identification process for a moving-direction plane of an observed region, the identification process being performed by an image processing unit of the medical image processing apparatus according to the first embodiment performs.

An identification process for a moving-direction plane of an observed region shown in step ST2 will be described in detail using a flowchart showing a subroutine for the identification process performed by the image processing unit 12 of the medical image processing apparatus 1 in the first embodiment.

FIG. 3 is a flowchart showing an example of the identification process for the moving-direction plane of an observed region, the identification process being performed by the image processing unit 12 of the medical image processing apparatus 1 according to the first embodiment.

Upon acquiring plural volume data from the storage unit 11, the image processing unit 12 of the medical image processing apparatus 1 causes the region identification unit 14 to identify voxel regions which represent an observed region in each item of the acquired volume data (step ST11).

Figure 4A:
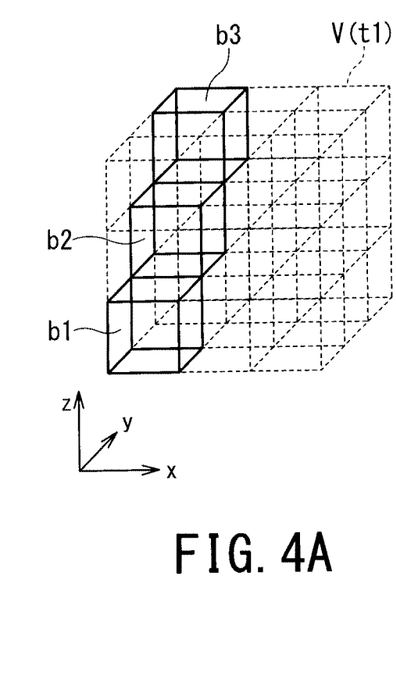
FIGS. 4A to 4C are schematic diagrams of voxel regions identified by a region identification unit of the medical image processing apparatus according to the first embodiment.
Figure 4B:
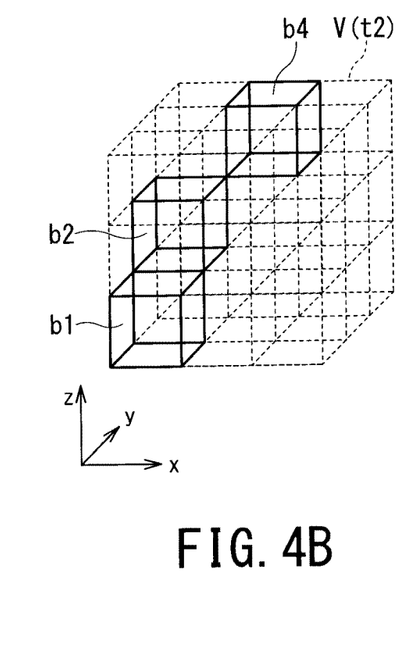
Figure 4C:
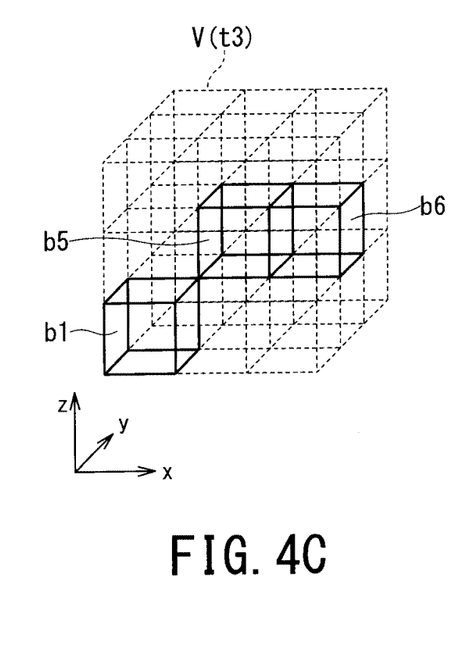

FIGS. 4A to 4C are schematic diagrams of voxel regions identified by the region identification unit 14 of the medical image processing apparatus 1 according to the first embodiment.

In the first embodiment, it is assumed, for example, that the medical image processing apparatus 1 acquires, from the medical diagnostic apparatus 2, three volume data V(t1), V(t2), V(t3) collected in time phases t1, t2, t3. Note that the time phases take place in the order t1, t2, t3, with t1 being the oldest and t3 being the newest. Also, in the first embodiment, it is assumed that each item of volume data V(t1), V(t2), or V(t3) has three voxel lines each in x, y, and z directions orthogonal to one another for a total of 27 voxels as shown in FIGS. 4A to 4C.

Furthermore, in the first embodiment, by taking a movement between adjacent voxels as one unit, unit vectors corresponding to the x, y, and z directions are denoted by i, j, and k, respectively. In this case, the right direction in FIG. 4A indicated by an arrow is designated as a positive x direction, the depth direction is designated as a positive y direction, and the upward direction is designated as a positive z direction.

For example, if volume data is collected by an X-ray computerized tomography apparatus, X-rays detected after passing through an observed region and X-rays detected without passing through the observed region differ in intensity. That is, in the volume data, the voxels which represent the observed region differ significantly in voxel values from the voxels which do not represent the observed region.

The region identification unit 14 selects, for example, only the voxels having a voxel value equal to or larger than a predetermined value and thereby identifies voxel regions which represent the observed region (step ST11).

In the first embodiment, it is assumed that three voxel regions identified in the volume data V(t1) are voxels b1, b2, and b3, respectively. Also, it is assumed that three voxel regions identified in the volume data V(t2) are voxels b1, b2, and b4, respectively. Also, it is assumed that three voxel regions identified in the volume data V(t3) are voxels b1, b5, and b6, respectively.

Note that in the first embodiment, the observed region depicted by the voxel b1 in the volume data V(t1), observed region depicted by the voxel b1 in the volume data V(t2), and observed region depicted by the voxel b1 in the volume data V(t3) are anatomically identical. Also, the observed region depicted by the voxel b2 in the volume data V(t1), observed region depicted by the voxel b2 in the volume data V(t2), and observed region depicted by the voxel b5 in the volume data V(t3) are anatomically identical. Also, the observed region depicted by the voxel b3 in the volume data V(t1), observed region depicted by the voxel b4 in the volume data V(t2), and observed region depicted by the voxel b6 in the volume data V(t3) are anatomically identical.

Note that the identification of voxel regions which represent an observed region is simply a process used to find the displacement among some or all of the voxel regions which represent the observed region and is not limited to the method described herein.

The moving direction identification unit 15 of the medical image processing apparatus 1 selects at least two of plural volume data (step ST12).

For example, from the volume data inputted to the image processing unit 12 from the medical diagnostic apparatus 2, the moving direction identification unit 15 selects the volume data collected in the oldest time phase and the volume data collected in the newest time phase. That is, in the first embodiment, the volume data V(t1) and volume data V(t3) are selected from among the volume data V(t1), V(t2), and V(t3).

Then, the moving direction identification unit 15 compares anatomically corresponding voxels among the voxel regions identified in step ST11, and calculates the displacement among the voxel regions (step ST13).

For example, in the first embodiment, that part of the observed region which is depicted by the voxel b1 of the volume data V(t1) shown in FIG. 4A remains unchanged in the volume data V(t3) shown in FIG. 4C, and thus the displacement is calculated as 0. Also, that part of the observed region which is depicted by the voxel b2 of the volume data V(t1) shown in FIG. 4A moves by +i in the interval between time phase t1 and time phase t3 and is depicted by the voxel b5 in the volume data V(t3) shown in FIG. 4 (C), and thus the displacement is calculated as +i. Similarly, that part of the observed region which is depicted by the voxel b3 of the volume data V(t1) shown in FIG. 4A moves by 2i-j-k in the interval between time phase t1 and time phase t3 and is depicted by the voxel b6 in the volume data V(t3) shown in FIG. 4 (C), and thus the displacement is calculated as 2i-j-k.

Out of the volume data used to calculate displacements, the moving direction identification unit 15 associates the calculated displacements with the respective voxels in the volume data collected in old time phases (step ST14). That is, in the first embodiment, the respective displacements calculated in step ST13 are associated with the respective voxels in the volume data V(t1) shown in FIG. 4A.

Figure 5:
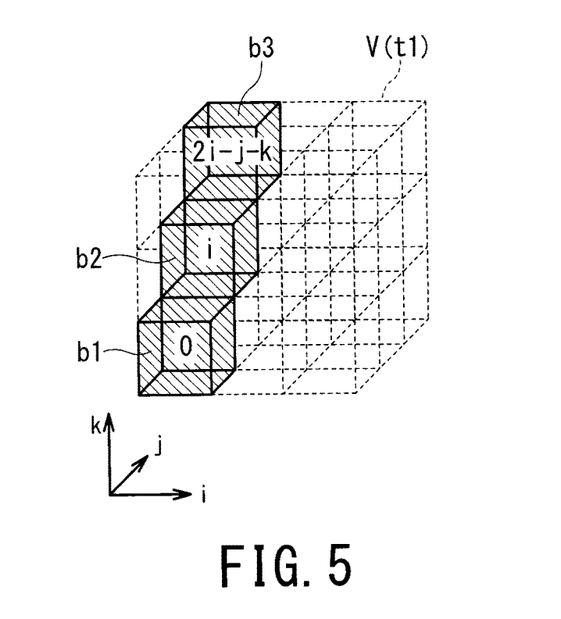
FIG. 5 is a schematic diagram showing calculated displacements and voxels associated with the displacements.

FIG. 5 is a schematic diagram showing calculated displacements and voxels associated with the displacements. As shown in FIG. 5, the voxel b1 in the volume data V(t1) is associated with a displacement of 0 calculated in step ST13. Also, the voxel b2 in the volume data V(t1) is associated with a displacement of i calculated in step ST13. The voxel b3 in the volume data V(t1) is associated with a displacement of 2i-j-k calculated in step ST13.

The moving direction identification unit 15 selects the voxel associated with the largest displacement and sets a vector which indicates the moving direction starting from the selected voxel (step ST15).

For example, since the largest of the displacements associated with the volume data V(t1) is the displacement of 2i-j-k associated with the voxel b3, the voxel b3 is selected in the first embodiment. The moving direction identification unit 15 sets, for example, a vector which indicates the moving direction of the observed region starting from a center of the voxel b3, in the volume data V(t1). In this case, the vector which indicates the moving direction of the observed region is the displacement of 2i-j-k corresponding to the voxel b3.

Also, the moving direction identification unit 15 selects the voxel associated with the smallest displacement and sets a rest point based on the selected voxel (step ST16).

Since the smallest of the displacements associated with the volume data V(t1) is the displacement of 0 associated with the voxel b1, the voxel b1 is selected in the first embodiment. The moving direction identification unit 15 sets, for example, a center of the voxel b1 in the volume data V(t1) as a rest point.

The moving direction identification unit 15 identifies the moving-direction plane of the observed region based on the vector set in step ST15 and the rest point set in step ST16 (step ST17).

In this case, the moving direction identification unit 15 identifies a plane formed by the set movement vector and rest point as the moving-direction plane of the observed region. Note that the plane formed here is not limited to a flat plane and may be a curved plane.

Figure 6:
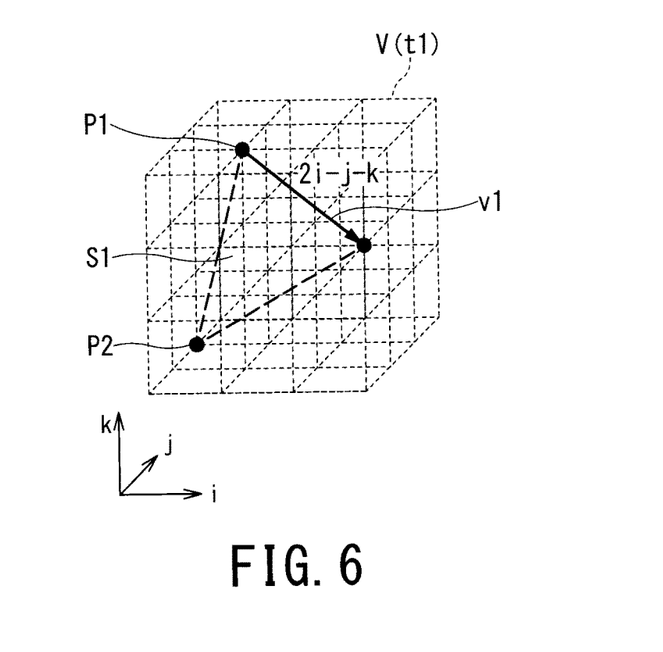
FIG. 6 is a schematic diagram showing a relationship among a vector which represents a moving direction, an initial point, a rest point, and a moving-direction plane.

FIG. 6 is a schematic diagram showing a relationship among a vector v1 which represents a moving direction, an initial point P1, a rest point P2, and a moving-direction plane S1. As shown in FIG. 6, the vector v1 which represents a moving direction starts from the center (initial point P1) of the voxel b3. The rest point P2 represents a center position of the voxel b1. The moving-direction plane S1 is formed by the vector v1 and rest point P2, where the vector v1 represents the moving direction.

When the moving-direction plane of the observed region is identified in step ST17 of FIG. 3, the display direction setting unit 16 goes to step ST3 of FIG. 2 and sets the identified moving-direction plane of the observed region as the display direction of the plural volume data.

As described above, the image processing unit 12 of the medical image processing apparatus 1 according to the first embodiment can set the display direction of a subject's observed region by performing the identification process for the moving-direction plane of the subject's observed region.

Note that although in the first embodiment described above, a series of image processing is performed by the image processing unit 12 of the medical image processing apparatus 1, this is not restrictive. For example, the medical image processing apparatus 1 may perform the series of image processing by the control unit 10 executing a program stored in the storage unit 11.

Also, although in the first embodiment described above, the medical diagnostic apparatus 2 is an X-ray computerized tomography apparatus, the medical diagnostic apparatus may be any other type as long as the medical diagnostic apparatus can generate the volume data defined in the embodiment of the present invention.

Also, although in the first embodiment described above, one moving-direction plane is identified based on the volume data collected in the oldest time phase and the volume data collected in the newest time phase, this is not restrictive.

For example, plural moving-direction planes may be identified based on the displacement between each pair of volume data items located next to each other in a time-phase direction, and the display direction for each volume data item may be changed based on the plural moving-direction planes.

Figure 7:
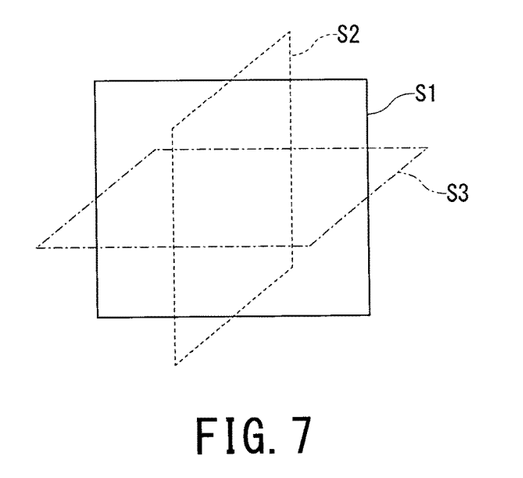
FIG. 7 is a schematic diagram showing an example of a display direction of volume data.

FIG. 7 is a schematic diagram showing an example of the display direction of volume data. Although in the first embodiment described above, the display direction is set to a direction perpendicular to the moving-direction plane identified by the moving direction identification unit 15, this is not restrictive. For example, as shown in FIG. 7, the display direction may be set to a direction perpendicular to a plane S2 (plane indicated by a dashed line) or a plane S3 (plane indicated by alternate long and short dashed lines) perpendicular to the moving-direction plane S1 (plane indicated by a solid line) identified by the moving direction identification unit 15.

Figure 8:
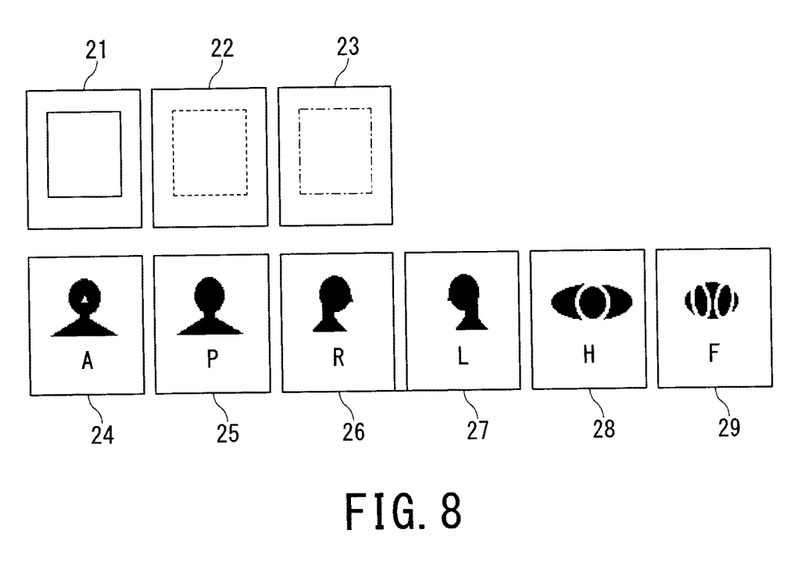
FIG. 8 is a schematic diagram of an input screen used to change the display direction of volume data.

FIG. 8 is a schematic diagram of an input screen used to change the display direction of volume data. For example, switch buttons 21 to 29 are displayed on a display screen of the display device 4.

For example, when the operator specifies the switch button 21 on the display device 4 using a mouse configuring the input device 3, the display direction is set to a direction perpendicular to the moving-direction plane S1 shown in FIG. 7. Also, when the operator specifies the switch button 22 on the display device 4 using the mouse configuring the input device 3, the display direction is set to a direction perpendicular to the plane S2 shown in FIG. 7. Also, when the operator specifies the switch button 23 on the display device 4 using the mouse configuring the input device 3, the display direction is set to a direction perpendicular to the plane S3 shown in FIG. 7.

Also, when the operator specifies the switch button 24 on the display device 4 using the mouse configuring the input device 3, the display direction is set to a direction viewed from the front of the subject. Also, when the operator specifies the switch button 25 on the display device 4 using the mouse configuring the input device 3, the display direction is set to a direction viewed from the back of the subject. Also, when the operator specifies the switch button 26 on the display device 4 using the mouse configuring the input device 3, the display direction is set to a direction viewed from the right side of the subject. Also, when the operator specifies the switch button 27 on the display device 4 using the mouse configuring the input device 3, the display direction is set to a direction viewed from the left side of the subject. Also, when the operator specifies the switch button 28 on the display device 4 using the mouse configuring the input device 3, the display direction is set to a direction viewed from the head of the subject. Also, when the operator specifies the switch button 29 on the display device 4 using the mouse configuring the input device 3, the display direction is set to a direction viewed from the legs of the subject.

In this way, volume data can be displayed from various directions, allowing a wide variety of observed regions to be displayed. Note that the switch buttons 21 to 29 are not limited to those displayed on the display screen, and may be provided as hardware.

Although in the first embodiment, description has been given of a case in which images subjected to a so-called volume rendering process are displayed as the display direction set to a direction perpendicular to the moving-direction plane S1, for example, a tomographic image of the moving-direction plane S1 may be displayed. Alternatively, MPR (Multi Planar Reconstruction) images including a tomographic image perpendicular to the moving-direction plane S1 may be displayed.

This improves clinical utility of the medical image processing apparatus 1 according to the first embodiment.

Although in the first embodiment, description has been given of a case in which voxel regions are identified in all the volume data transferred to the image processing unit 12 from the storage unit 11 of the medical image processing apparatus 1, this is not restrictive. For example, voxel regions may be identified only in the volume data used to calculate displacement.

Also, although in the first embodiment, description has been given of a case in which the voxel regions which represent the entire observed region in the volume data are identified, this is not restrictive. For example, displacement may be calculated by identifying only anatomically identical single voxels in an observed region or voxels of plural feature points. This improves, for example, image processing speed of the medical image processing apparatus 1 according to the first embodiment.

Although in the first embodiment described above, of the plural volume data transferred to the storage unit 11 from the medical diagnostic apparatus 2, the volume data collected in the oldest time phase and the volume data collected in the newest time phase are used to calculate displacement, this is not restrictive. For example, the volume data used to calculate displacement may be determined selectively by the operator. Alternatively, the displacement may be calculated using volume data other than the volume data collected in the oldest time phase and volume data collected in the newest time phase.

Although in the first embodiment, description has been given of a case in which plural volume data are transferred to the storage unit 11 from the medical image processing apparatus 2 via operator input, this is not restrictive. For example, collected volume data may be transferred automatically from outside or the volume data to be transferred may be determined by the medical diagnostic apparatus 2.

Also, although in the first embodiment, description has been given of a case in which displacement of voxels between volume data items is calculated to identify the moving-direction plane S1, this is not restrictive. For example, the moving-direction plane may be identified using a method as described in detail below.

(Modification)

FIGS. 9A to 9C and 10 are schematic diagrams showing a method for identifying a moving-direction plane based on a simplified model of an observed region as depicted in volume data, as a modification.

Figure 9A:
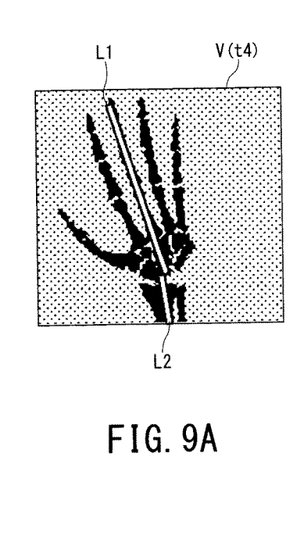
FIGS. 9A to 9C are schematic diagrams showing a method for identifying the moving-direction plane based on a simplified model of an observed region depicted in volume data, as a modification.
Figure 9B:
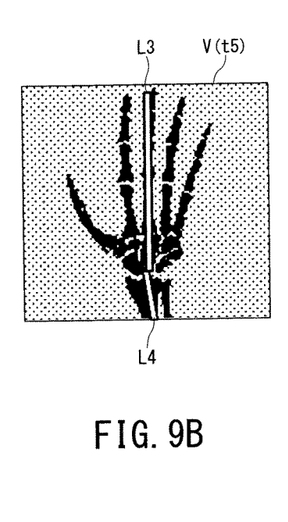
Figure 9C:
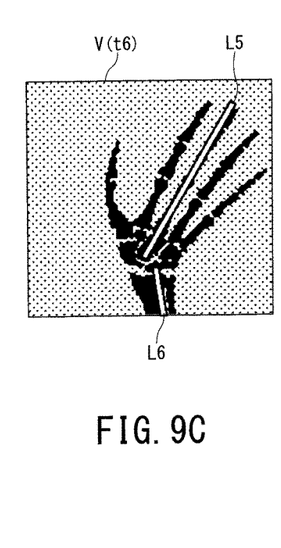

In the present modification, as shown in FIGS. 9A to 9C, for example, a subject's wrist and its surroundings depicted as an observed region in volume data is represented in a simplified manner by a thin line running through a center of the subject's middle finger and a thin line running through a center of the subject's forearm.

In the present modification, it is assumed that three volume data V(t4), V(t5), V(t6) are collected in time phases t4, t5, t6, restrictively. Also, the time phases t4, t5, t6 occur in this order, with t4 being the oldest time phase and t6 being the newest time phase. In FIGS. 9A to 9C, thin lines L1, L3, L5 indicate the thin line running through the center of the subject's middle finger while thin lines L2, L4, L6 indicate the thin line running through the center of the subject's forearm.

Figure 10:
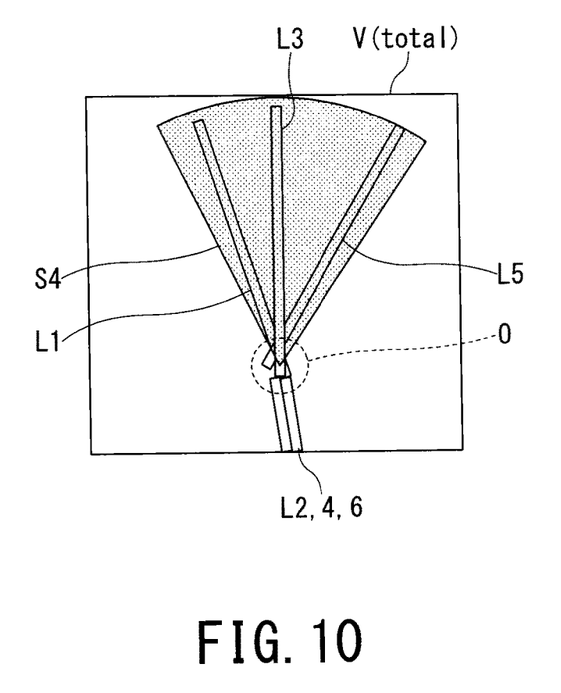
FIG. 10 is schematic diagram showing a method for identifying a plane including a moving direction based on the simplified model of the observed region depicted in volume data, as the modification.

In the present modification, as shown in FIG. 10, the moving direction identification unit 15 generates a single item of volume data V(total) by superimposing the thin lines L1 to L6 which represent the observed region shown in a simplified manner. Then, as shown in FIG. 10, the moving direction identification unit 15 determines, based on traces of the thin lines L1 to L6 shown in the volume data V(total), that movement of the observed region between time phase t4 and time phase t6 constitutes a rotary motion performed on a plane S4 around a center portion O of the wrist, and identifies the plane S4 as a moving-direction plane.

Also, although a medical image processing apparatus has been described in the first embodiment, the embodiment of the present invention is not limited to this and is also applicable as a medical diagnostic apparatus having the functions of the medical image processing apparatus shown in the first embodiment. As an example, description will be given of a case in which the medical diagnostic apparatus is an X-ray computerized tomography apparatus.

Second Embodiment

Figure 11:
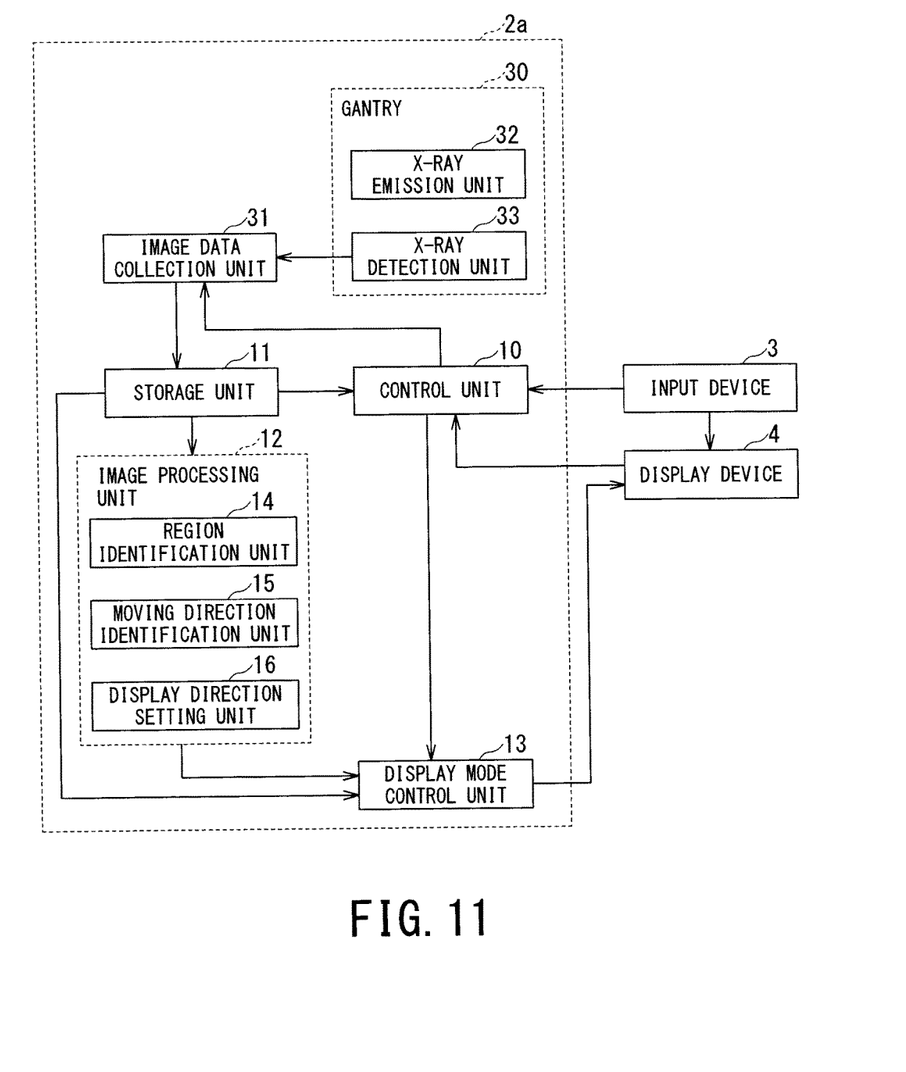
FIG. 11 is a block diagram of an X-ray computerized tomography apparatus according to a second embodiment.

FIG. 11 is a block diagram of an X-ray computerized tomography apparatus 2a according to a second embodiment. The X-ray computerized tomography apparatus 2a has the functions of the medical image processing apparatus 1 shown in the first embodiment. That is, the X-ray computerized tomography apparatus 2a according to the second embodiment includes the control unit 10, the storage unit 11, the image processing unit 12, and the display mode control unit 13, which are configuration of the medical image processing apparatus 1 shown in the first embodiment, and further comprises a gantry 30 and an image data collection unit 31.

The gantry 30 has a function to rotate an X-ray emission unit 32 and an X-ray detection unit 33 with the X-ray emission unit 32 and X-ray detection unit 33 kept facing each other. The X-ray computerized tomography apparatus 2a is connected with the input device 3 and display device 4 by a wired or wireless method and configured to be able to exchange data and signals with these devices.

The X-ray emission unit 32 has a function to emit X-rays according to instructions from the input device 3 via the control unit 10.

The X-ray detection unit 33 has a function to detect X-rays emitted from the X-ray emission unit 32 and transmitted through the subject including the observed region, convert the X-rays into a signal, and send the resulting signal to the image data collection unit 31.

The image data collection unit 31 has a function to collect volume data including an examination region of the subject for each time phase on a basis of the signal received from the X-ray detection unit 33.

Note that with the X-ray computerized tomography apparatus 2a according to the second embodiment, for example, the plural volume data collected are transferred from the image data collection unit 31 and stored in the storage unit 11, each volume data of the plural volume data being collected for each time phase. Also, the X-ray computerized tomography apparatus 2a according to the second embodiment is designed, for example, such that instructions are transmitted to the control unit 10 from the display device 4 via the input device 3, eventually instructing the image data collection unit 31 to transmit volume data.

Furthermore, the X-ray computerized tomography apparatus 2a according to the second embodiment is designed, for example, such that when the volume data transferred from the image data collection unit 31 is stored in the storage unit 11, the control unit 10 instructs the storage unit 11 to transfer the transferred volume data to the image processing unit 12.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
    processing circuitry configured to
        identify at least two bone regions, each bone region included in a corresponding volume data of a plurality of volume data, the plurality of volume data each including respective bone regions each depicting a bone, each of the plurality of volume data being collected at a corresponding time phase,
        identify, from the volume data, a moving direction of the bone based on the at least two bone regions, and
        set a display direction of the plurality of volume data based on the identified moving direction.

2. The medical image processing apparatus according to claim 1, wherein the processing circuitry is further configured to identify the moving direction based on a displacement of the at least two bone regions.

3. The medical image processing apparatus according to claim 1, wherein the processing circuitry is further configured to
    identify voxel regions which represent part or all of each of the at least two bone regions,
    calculate displacements of some or all of the voxel regions between the at least two of the plurality of volume data in which the voxel regions have been identified, and
    identify the moving direction based on the calculated displacements.

4. The medical image processing apparatus according to claim 1, wherein the processing circuitry is further configured to
    identify voxel regions which represent part or all of each of the at least three bone regions,
    in the volume data in which voxel regions have been identified, calculate displacements of some or all of the voxel regions between each pair of volume data items located next to each other in a time-phase direction, and
    identify the moving direction based on each of at least two of the calculated displacements.

5. The medical image processing apparatus according to claim 3, wherein the processing circuitry is further configured to identify a plane formed by a displacement vector of a voxel which represents the largest displacement and a voxel which represents the smallest displacement as a plane containing the moving direction, the largest and smallest displacements being included in the calculated displacements between the two volume data.

6. The medical image processing apparatus according to claim 4, wherein, the processing circuitry is further configured to identify a plane formed by a displacement vector of a voxel which represents the largest displacement and a voxel which represents the smallest displacement as a plane containing the moving direction, the largest and smallest displacements being included in the calculated displacements between the two volume data.

7. The medical image processing apparatus according to claim 1, wherein the processing circuitry is further configured to identify a plane containing the moving direction based on models indicating the bone regions included in the respective at least two volume data.

8. The medical image processing apparatus according to claim 1, wherein the processing circuitry is further configured to
    cause a display to display image data,
    set a direction perpendicular to a plane containing the moving direction as the display direction of the plurality of volume data, and
    cause the display to display at least one of the plurality of volume data as the display image data located in the display direction.

9. The medical image processing apparatus according to claim 1, wherein the processing circuitry is further configured to cause a display to display a tomographic image as a display image on a plane containing the identified moving direction.

10. A medical image processing apparatus comprising:
    processing circuitry configured to
        identify at least two bone regions, each bone region included in a corresponding volume data of a plurality of volume data, the plurality of volume data each including respective bone regions each depicting a bone of a subject, each of the plurality of volume data being collected at a corresponding time phase;
        identify, from the volume data, a moving direction of the bone based on the at least two bone regions; and
        cause a display to display a tomographic image as a display image on a plane containing the identified moving direction.

11. An X-ray computerized tomography apparatus, comprising:
- an image data collection apparatus equipped with an X-ray source and an X-ray detector rotatable with respect to each other and facing each other, and configured to collect a plurality of volume data based on X-rays emitted from the X-ray source, and detected by the X-ray detector, during rotation of the X-ray source and the X-ray detector, the plurality of volume data including respective bone regions each depicting a bone, each of the plurality of volume data being collected at a corresponding time phase;
- a memory configured to store the plurality of volume data collected by the image data collection unit; and
- processing circuitry configured to
    - identify at least two bone regions, each bone region included in a corresponding volume data of the plurality of volume data,
    - identify, from the volume data, a moving direction based on the at least two bone regions, and
    - set a display direction of the plurality of volume data based on the identified moving direction.

12. The X-ray computerized tomography apparatus according to claim 11, wherein the processing circuitry is further configured to
- identify voxel regions which represent part or all of each of the at least two bone regions,
- calculate displacements of some or all of the voxel regions between the at least two of the plurality of volume data in which the voxel regions have been identified, and
- identify the moving direction based on the calculated displacements.

13. The X-ray computerized tomography apparatus according to claim 11, wherein the processing circuitry is further configured to identify voxel regions which represent part or all of each of at least three bone regions, and
- in the volume data in which voxel regions have been identified, calculate displacements of some or all of the voxel regions between each pair of volume data items located next to each other in a time-phase direction, and identify the moving direction based on each of at least two of the calculated displacements.

14. The X-ray computerized tomography apparatus according to claim 12, wherein the processing circuitry is further configured to identify a plane formed by a displacement vector of a voxel which represents the largest displacement and a voxel which represents the smallest displacement as a plane containing the moving direction, the largest and smallest displacements being included in the calculated displacements between the two volume data.

15. The X-ray computerized tomography apparatus according to claim 13, wherein the processing circuitry is further configured to identify a plane formed by a displacement vector of a voxel which represents the largest displacement and a voxel which represents the smallest displacement as a plane containing the moving direction, the largest and smallest displacements being included in the calculated displacements between the two volume data.

16. A medical image processing method, comprising:
- identifying at least two bone regions, each bone region included in a corresponding volume data of a plurality of volume data, the plurality of volume data each including respective bone regions each depicting a bone, each of the plurality of volume data being collected at a corresponding time phase;
- identify, from the volume data, a moving direction of the bone based on the at least two bone regions; and
- setting a display direction of the plurality of volume data based on the identified moving direction.

* * * * *